United States Patent [19]
Cowan

[11] Patent Number: 5,740,812
[45] Date of Patent: Apr. 21, 1998

[54] APPARATUS FOR AND METHOD OF PROVIDING BRAINWAVE BIOFEEDBACK

[75] Inventor: Jonathan D. Cowan, Goshen, Ky.

[73] Assignee: Mindwaves, Ltd., Goshen, Ky.

[21] Appl. No.: 590,405

[22] Filed: Jan. 25, 1996

[51] Int. Cl.$^6$ ........................................................ A61B 5/04
[52] U.S. Cl. ........................................... 128/732; 128/641
[58] Field of Search ........................... 128/630, 639–641, 128/643–644, 696, 710, 731–732, 905; 600/26–27; 607/139

[56] References Cited

U.S. PATENT DOCUMENTS

| | | | |
|---|---|---|---|
| 3,490,439 | 1/1970 | Rolston | 128/2.1 |
| 3,508,541 | 4/1970 | Westbrook et al. | 128/2.1 |
| 3,998,213 | 12/1976 | Price | 128/2.1 |
| 4,033,334 | 7/1977 | Fletcher et al. | 128/2.1 |
| 4,311,152 | 1/1982 | Modes et al. | 128/641 |
| 4,537,198 | 8/1985 | Corbett | 128/639 |
| 5,209,494 | 5/1993 | Spector | 273/460 |
| 5,295,491 | 3/1994 | Gevins | 128/732 X |
| 5,306,228 | 4/1994 | Rubins | 600/27 |
| 5,348,006 | 9/1994 | Tucker | 128/639 |
| 5,377,100 | 12/1994 | Pope et al. | 364/410 |
| 5,406,957 | 4/1995 | Tansey | 128/732 |
| 5,409,445 | 4/1995 | Rubins | 600/27 |
| 5,645,063 | 7/1997 | Straka, Jr. | 128/641 |

*Primary Examiner*—Jennifer Bahr
*Assistant Examiner*—Ryan Carter
*Attorney, Agent, or Firm*—Middleton & Reutlingen; James C. Eaves, Jr.

[57] ABSTRACT

The present invention relates to an apparatus for and a method of providing brainwave biofeedback to a user while the user is simultaneously doing other tasks, for example, while the user is responding to a computer learning lab, working with another computer program, or playing a game. For example, a user could wear a headphone sensor unit, a virtual reality headset sensor unit, or a similar enclosure incorporating sensors made of comfortable compound sponges soaked in an electrolyte solution. The unit can detect brainwave signals which are then processed and interfaced with a computer. Audio and/or video feedback is provided to the user which indicates the user's focus or alertness. While the sensor unit could have therapeutic uses, the current embodiments relate to educational and recreational uses and for uses related to increasing personal performance.

20 Claims, 3 Drawing Sheets

5,740,812

APPARATUS FOR AND METHOD OF PROVIDING BRAINWAVE BIOFEEDBACK

BACKGROUND OF THE INVENTION

1. Field of the Invention

The present invention relates to an apparatus for and a method of providing brainwave biofeedback to a user while the user is simultaneously doing other tasks, for example, while the user is responding to a computer learning lab, working with another computer program, or playing a game. For example, a user could wear a headphone sensor unit, a virtual reality headset sensor unit, or a similar enclosure incorporating sensors comprised of comfortable compound sponges soaked in an electrolyte solution. The unit can detect brainwave signals which are then processed and interfaced with a computer. Audio and/or video feedback is provided to the user which indicates the user's focus or alertness. While the sensor unit could have therapeutic uses, the current embodiments relate to educational and recreational uses and for uses related to increasing personal performance.

2. Discussion of the Prior Art

The brain produces monitorable signals of from at least 1–40 Hertz (Hz). Signals of from about 1–4 Hz indicate a deep sleep state (delta); signals of from about 4–8 Hz indicate a reverie or daydreaming state (theta); signals of from about 8–13 Hz indicate an alert, but less mentally busy state (alpha); and, signals above 13 Hz indicate a vigilant state (beta).

U.S. Pat. No. 3,998,213, to Price, teaches a self-adjusting holder for automatically positioning electroencephalographic ("EEG") electrodes. U.S. Pat. No. 4,537,198, to Corbett, teaches an electrode cap. U.S. Pat. No. 5,348,006, to Tucker, teaches a head positioning pedestal.

U.S. Pat. No. 5,406,957, to Tansey, teaches an apparatus and method for monitoring, analyzing, and utilizing brainwave data.

SUMMARY OF THE INVENTION

The present invention is for an apparatus and a method of detecting and providing instantaneous brainwave biofeedback so that a user can monitor his or her own level of focus or concentration or for monitoring by others, such as a parent or teacher. For example, while a student is using a computer to learn, brainwave signals are monitored and processed to provide immediate feedback on the same computer monitor to show the user at least one indicator of focus. Examples of indicators include an instantaneous EEG, a short-term concentration score, and a long-term concentration index. New methods of processing of brainwave signals are taught.

Processed brainwave signals can be used as input to a separate program, running with any other computer program or activity where the indicator can be displayed. For example, if the user is "surfing" the INTERNET, brainwave feedback could be provided on a "thermometer" or "gas" gauge. Alternatively, the processed brainwave signals can be incorporated into another program. For example, if a user was playing a computer or video game, the better the user's focus, the more in focus the screen, the poorer the user's focus, the more out of focus the screen. Other screen adjustments could be made, such as changing the screen contrast, or the audio heard by the user could be varied. With a virtual reality helmet, brainwave feedback could be used to impact what the player sees and hears.

To provide brainwave signals, a headset or virtual reality helmet with enhanced detection and a signal processing interface, for example, to a computer, can be provided.

The brainwave sensor of this invention has been designed to provide easy to use, long-lasting, comfortable contact with the user's scalp and ears. The headset or helmet of the present invention may comprise a headband having at least one earpiece connected thereto, the earpiece having an ear pad, the ear pad having a sensor receiving receptacle therein, the sensor receiving receptacle having an ear lobe sensor unit detachably received therein, the ear lobe sensor unit and respective wearer's ear lobe being in a flush relation, the ear lobe sensor unit including an electrode having an electrode lead extending therefrom, and where the headband detachably receives a pair of scalp sensor units, each scalp sensor unit including an electrode having an electrode lead extending therefrom. Preferably, the scalp sensor unit includes a specially constructed compound sponge providing a flush relationship with the user's scalp through the hair, and simplified cleaning of dead skin from the scalp to facilitate electrical connections.

Further, the present invention comprises a brainwave biofeedback apparatus to be worn by a user on the user's head, the apparatus having a scalp portion passing over a scalp portion of the user's head, the apparatus further comprising at least one scalp sensor unit, the at least one scalp sensor unit being detachably receivable by the scalp portion, the at least one scalp sensor unit having a scalp electrode cup and a compound sponge assembly, the scalp electrode cup including a scalp electrode having a scalp electrode lead extending therefrom, the compound sponge assembly including an absorbent sponge portion and a scalp contact and cleaning portion, the scalp contact and cleaning portion to engage said user's hair, the absorbent sponge portion being partway received by the scalp electrode cup. This apparatus can also include at least one earpiece having an ear pad, the ear pad having a sensor receiving receptacle therein, the sensor receiving receptacle having an ear lobe sensor unit detachably received therein, the ear lobe sensor unit having a lobe electrode cup and a lobe sponge, the lobe electrode cup including a lobe electrode having a lobe electrode lead extending therefrom, the lobe sponge including an ear lobe engaging portion, the lobe sponge being partway received by said lobe electrode cup.

BRIEF DESCRIPTION OF THE DRAWINGS

A better understanding of the invention will be had upon reference to the following description in conjunction with the accompanying drawings in which like numerals refer to like parts and wherein.

DETAILED DESCRIPTION OF THE PREFERRED EMBODIMENT

Figure 1:
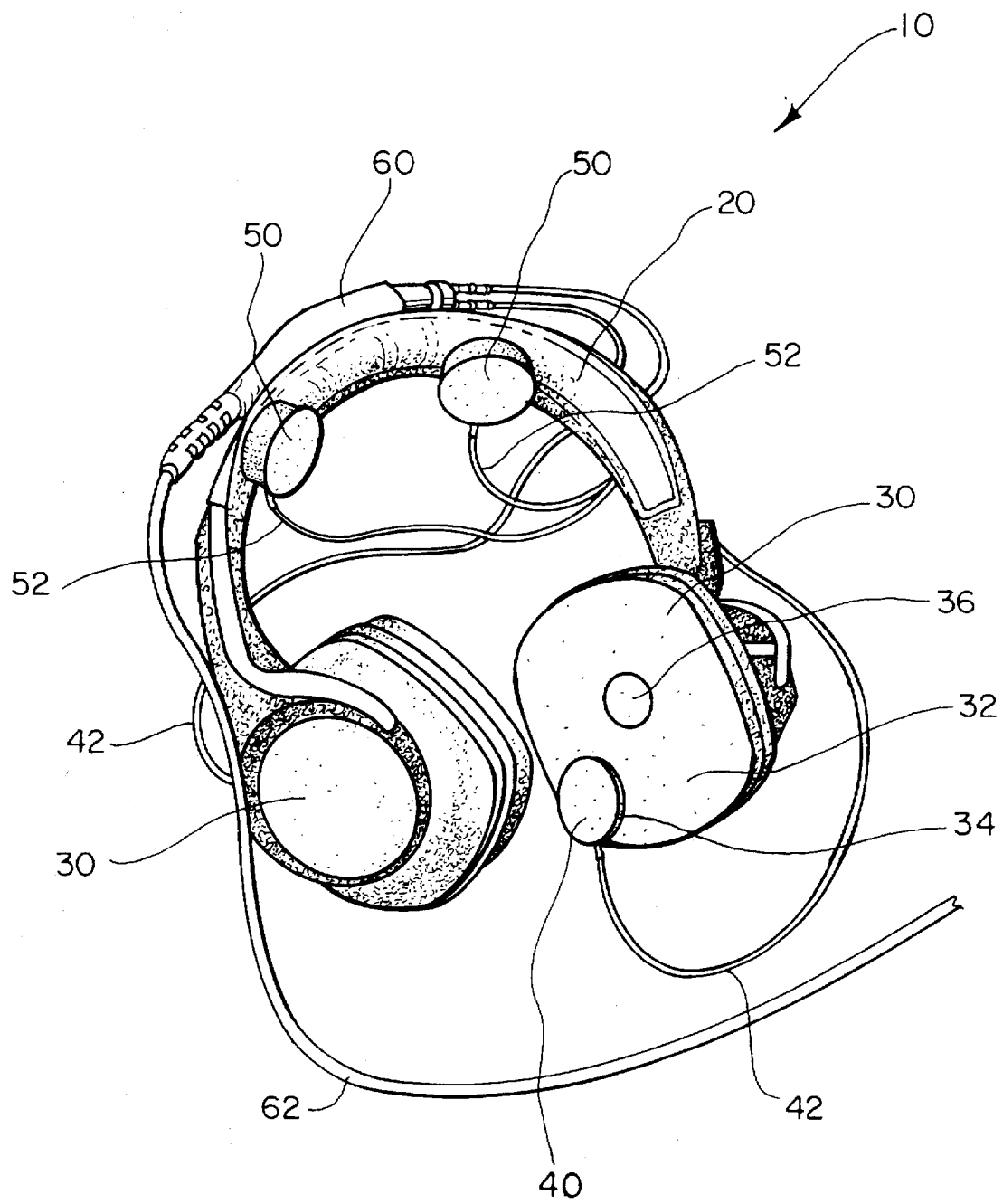
FIG. 1 is a perspective view of a headset of the present invention incorporating ear lobe sensor units and scalp sensor units.
Figure 2:
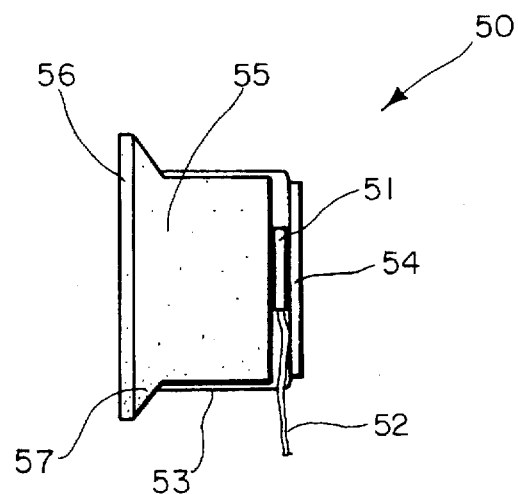
FIG. 2 is a cross-section view of a scalp sensor unit.
Figure 3:
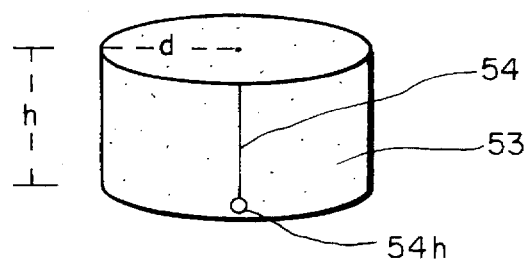
FIG. 3 is a perspective view of an electrode cup.
Figure 4:
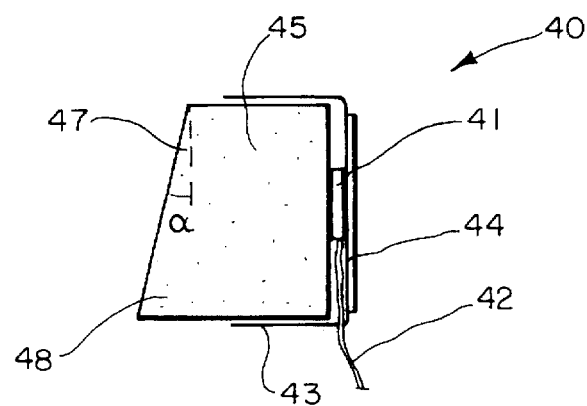
FIG. 4 is a cross-section view of a ear lobe sensor unit.

With reference to FIGS. 1–4, a headset 10 and its ear lobe sensor units 40 and scalp sensor units 50 are shown. Headset 10 includes a headband 20 and a pair of earpieces 30, although a single earpiece could be used. Each earpiece 30 has a pad 32 with a headphone speaker 36 therein. Headphone speakers can provide an audio signal to a wearer, as in any conventional headphone. As desired, the brainwave signals can be detected and amplified and processes can be used to affect what the wearer hears through speakers 36.

Pad 32 has a recessed portion 34 at a location where the pad would engage a wearer's ear lobe. An ear lobe sensor unit 40 fits within recessed portion 34. The geometry of the ear lobe engaging portion of unit 40 ensures that ear lobe sensor unit 40 has maximum contact with the wearer's ear lobe. Alternatively, other locations on the ear may be contacted by specially shaped sponges or an ear pad made from conducting sponge, foam, or other electrical conducting material covering a larger portion of the ear.

Sensor units 40 and 50 have respective electrode leads 42 and 52 which are received by input/output interface unit 60, which also receives input/output cable 62. Input/output cable 62 is, for example, connected to a biofeedback processor or computer serial port. Unit 60 may, for example, include signal processing circuitry.

Scalp sensor unit 50 includes an electrode cup 53 having, for example, a diameter "d" of about one inch (2.5 cm) and a height "h" of about ⅝ inch (1.6 cm). This height provides a "deep well" for retaining moisture in a cosmetic sponge 55 received partway therein. Cup 53 could have a lid placed thereover. The lid would have an opening therein through which sponge 55 would extend outward. The lid would help prevent drops of moisture from dripping on the wearer of headset 10.

Electrode cup 53 has a slit 54 terminating in a hole 54h to permit an electrode lead 52 to be received by cup 53. Cup 53 is shown having an electrode 51 received therein with an electrode lead 52 extending therefrom. Strain relief, such as shrink wrap, not shown, can be provided around lead 52 where it passes tightly through slit hole 54h. While electrode 51 is shown positioned against the cup bottom, other electrode positioning is envisioned.

Cup 53 securely receives a cosmetic sponge 55, which may be a dense rubber or latex. A firm structured sponge is desired to retain shape. For example, red rubber sponge by A. J. Siris Products Corporation of Patterson, New Jersey has a desired structure. Sponge 55 and sponge 45, explained later, will absorb enough salt water to be effective for over three hours. Alternatively, cup 53 can include an opening so that salt water can be added during use, or headset 10 can include a salt water reservoir with tubes to provide salt water to sponges 55 and 45. Alternatively, a reservoir could be provided within each cup 53.

Sponge 55 is shown having a larger portion 57 external of cup 53. Scalp sensor unit 50 generally engages the hair of a wearer. To improve connectivity, sponge 55 has a woven fiber portion 56 attached thereto. For example, the fiber scrub portion of a no-scratch scrub sponge by 3M under the trademarked name "SCOTCH-BRITE", catalog number 520/521, when placed on the scalp and moved back and forth, has been found to effectively penetrate the hair and remove dead scalp skin cells to improve electrical connectivity.

Cup 53 is shown having a hook and loop type fastener 54, such as the trademarked separable fastener material "VELCRO", attached outside the cup bottom. This is used to attach the scalp sensor unit 50 to headband 20 at a desired location, which will vary with different users. Being able to remove the cups permits rewetting of the sponges. Other attachment means are envisioned. For example, fastener 54 could be replaced with a snap. A plurality of snap receivers could be attached to headband 20 and the cup 53 snapped into the desired receiver. If there is a lid on cup 53, the fiber portion 56 could be attached to the external portion of sponge 55.

Ear lobe sensor unit 40 has an electrode cup 43 which is similar to cup 53. As with unit 50, cup 43 receives an electrode 41 and has an electrode lead 42 extending therefrom. Fastener 44, for example, "VELCRO", is shown which may be used to secure cup 43 within sensor receiving receptacle 34. A snap or other attachment means may also be used.

Cosmetic sponge 45 is shown having a trapezoidal shaped cross-section. This shape permits maximum engagement with a wearer's ear lobe. The upper portion 47 engages the ear lobe cartilage and the wider lower portion 48 engages the lower, softer part of the ear lobe. Shown is the angle "$\alpha$" of approximately 15°. Alternatively, the sponge could be custom shaped to fit a desired place on the ear; for example, a U-shaped sponge could fit around the ear lobe cartilage.

Input/output interface unit 60 receives audio signal(s) through input/output cable 62 and provides those audio signal(s) to headphone speakers 36. While more or less electrodes can be employed as desired, each of the four electrodes 41/51 provides a signal to interface unit 60 through respective electrode lead 42/52. Processed or unprocessed electrode signals may be passed through cable 62. Cable 62 is preferably shielded. Also, instead of cable 62, radio waves, infrared light, or other transmission means may be employed to interface the headset 10 with, for example, the biofeedback processor. It is envisioned that programs contained in an EPROM or a computer will be used to make calculations and provide indications of alertness.

Electrodes 41/51 may be, for example, acrylonitrile-butadiene-styrene ("ABS") plastic impregnated with graphite and covered with silver/silver chloride, although, other electrode materials may be used. Cosmetic sponge 45/55, soaked in a saline or other electrolyte solution, conducts electricity to the electrodes from the ear lobe or scalp, as appropriate.

To demonstrate possible processing of the signals from the four electrodes 41/51, a signal from right ear lobe electrode 41 may be an electrically grounded signal, a signal from left ear lobe electrode 41 may be a neutral reference signal, a first signal "S1" from right head electrode 51 may be provided, and a second signal "S2" from left head electrode 51 may be provided. It is noted that the ear lobes are not the only place on the wearer's body to place ground and obtain a neutral reference signal; although placing all the electrodes into a headset or helmet is more convenient for the user. The in-phase components of signals S1 and S2 are added after pre-amplification. A particular low frequency band, DC to 12 Hertz or portions thereof, is extracted by digital or analog filtering or by a Fast Fourier Transform. A signal representing the magnitude or power of this output is divided by a similarly derived signal representing the magnitude or power for a wider frequency band, DC to at least 32 Hertz. This ratio, representing sleep and daydreaming brainwaves divided by total brainwaves, is then subtracted from or divided into a desired fixed number, for example, the number 32, with the resulting number providing a biofeedback indicator of increased alertness.

Instead of using the DC to 12 Hertz band, the ratio of a 12–128 Hertz band (or portions thereof) to a DC to 128 Hertz band (or portions thereof) can be evaluated to provide a biofeedback indicator of alert and vigilant brainwaves divided by total brainwaves. In this situation, the closer the ratio is to unity, the better the alertness of the testee, while the closer the ratio is to zero, the less the alertness of the testee.

Figure 5:
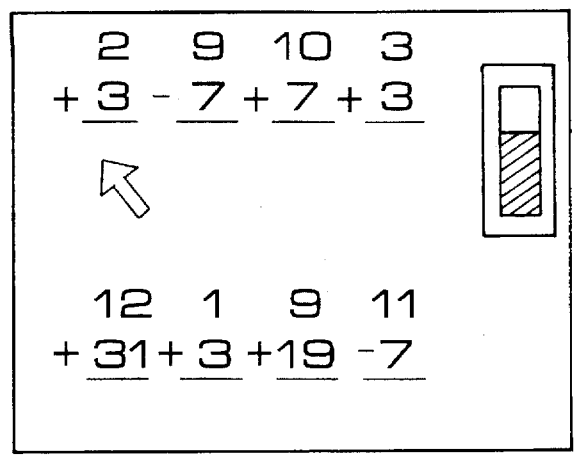
FIG. 5 is a representation of a computer monitor showing an educational game, the monitor displaying an indication of alertness.

This biofeedback indicator can be provided to a computer program through, for example, a serial or game port, so that the computer monitor provides an indication of alertness or lack thereof. For example, in a Windows environment, or a similar environment such as a Computer Learning Lab, an alertness program could be running along with an educational program. As seen in FIG. 5, a user is learning to add and subtract. A window designated by the numeral 2 is shown providing an indication of alertness. The alertness program will sample brainwaves at a sampling rate sufficient to provide real-time feedback, for example, at a sampling rate of twenty times per second. Instead of displaying the instantaneous values as the indication of alertness, the display can represent an average of values over a preselected time interval. As another possibility, the display can be differential, representing the change in alertness, either more or less alert at prior sessions or at prior times in the same session. The indication of alertness can also be used to provide audio feedback through headphone speakers 36, for example, by a volume change.

Statistical analysis can also be run on the raw or processed EEG data. For example, if a user was using a learning program for a thirty minute study session, indicators of alertness during the first ten minutes, middle ten minutes, and last ten minutes could be provided. Also, results for different study sessions could be compared and instantaneous indicators provided. Further, if used in a multiple student environment, indicators of alertness for each of the plurality of students could be simultaneously provided to a teacher's monitor.

Figure 6:
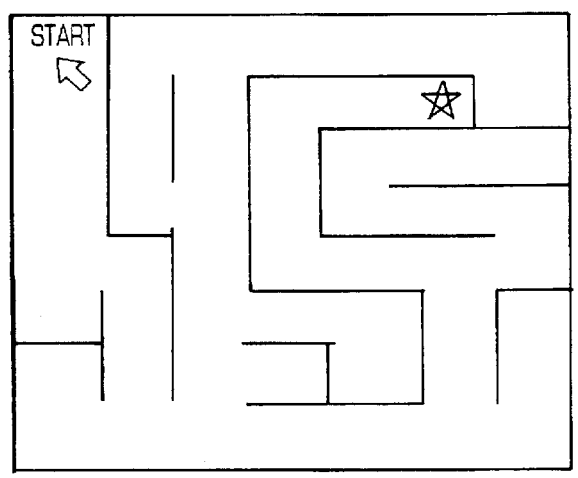
FIG. 6 is a representation of a computer monitor showing a maze to be solved by a user, the maze "in focus" because the user has a satisfactory alertness indicator.
Figure 7:
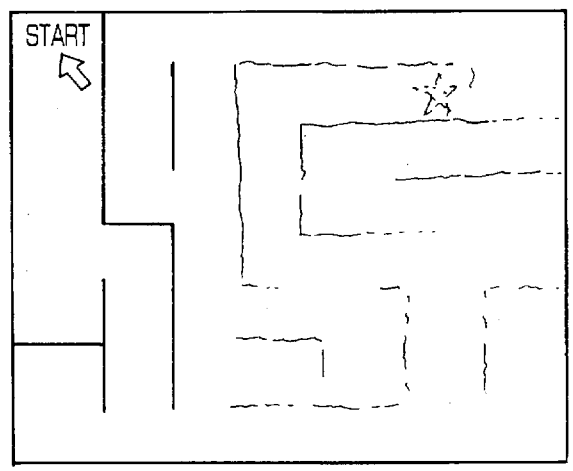
FIG. 7 is a representation of the computer monitor of FIG. 6 with portions "out of focus" because the user's alertness indicator is less that satisfactory.

Also, the alertness indicator can be incorporated directly into a computer program. FIG. 6 demonstrates a simple maze that a user must solve. As long as the user's alertness indicator is at a satisfactory level, the screen will be in focus as seen in FIG. 6. However, if while trying to solve the maze, the user's alertness indicator falls below a satisfactory level some or all of the maze will go out of focus, as seen in FIG. 7. Also, a fixed indicator number does not have to be used to set the out of focus condition. For example, assuming an alertness indicator range of zero to one, with one being the most alert, the monitor could be a total blur near zero, totally focused near one, and variable in between. For example, the screen would be more in focus at 0.7 than 0.6. Alternatively, or in addition, screen brightness, screen contrast, percentage of total image displayed, and/or the volume, clarity, or characteristics of audio output can be varied based upon the alertness indicator.

Further, an indication of alertness can be processed by a video interface, which further transforms the output of a video adaptor board as a function of the alertness indicator, such that, for example, a user playing a video game, could have game play affected by the alertness indicator, in manners similar to those described above, without changing the video game program.

Other processing of the brainwave signals is envisioned. For example, the EEG derived from two sites on the head, for example, C3 and C4 or Fz and Pz, and a neutral reference site, for example, the ear lobe, is amplified and filtered to eliminate low frequency artifacts by using a low frequency filter at about 2 Hertz. The two signals are then combined by digital or analog circuit means to form separate sum and difference signals, which respectively contain the in-phase and out-of-phase information from these signals. Software contained in an EPROM or computer program analyzes the resulting two signals by a Fast Fourier Transform and/or digital filtering into specified 1–34 Hertz bands, using, for example, a desired upper cut-off frequency. From the summed signals, the software then recombines selected frequency bands to form an in-phase low frequency signal with a pre-specified bandwidth comprising frequencies between 2 to 11 Hertz. From the difference signals, the software derives an out-of-phase high frequency signal, comprising some portion of the frequencies between 11 and 45 Hertz. The user would try to increase the out-of-phase high frequency EEG output and simultaneously inhibit the in-phase low frequency EEG output to enhance alertness.

As another example, it may be desired to analyze the brainwave signals, which are derived from a site or sites on the head and from a neutral reference, such as the ear lobe, from about 2 to 32 Hertz to provide a testee feedback to minimize emotional thoughts and feelings. Software contained in an EPROM or in a computer program calculates the frequency below which a preselected percentage ("N%") of EEG energy is contained. For example N can be in the range of 20% to 80%. Typically, the higher the frequency, the better the concentration, the lower the frequency, the better the relaxation. For example, with sensors located at the temporal area, for example, T3, T5, or F7, decreasing the frequency will minimize emotional thoughts and feelings. With this testing, additional or different scalp sensor units 50 may be employed at additional or different locations, such as for sampling at temporal or frontal areas of the brain. Plastic extensions from the headband 20 can be provided to facilitate placement.

Also, using an alertness indicator, a computer program can direct a user to attempt to change from one state of alertness to another. For example, assuming N of 60%, a user could be requested to concentrate on a preset screen display to have 60% of the brainwave energy above a frequency of 13 Hertz for a preselected time period. The time to achieve this criterion could be recorded. Then, the screen display could be changed to a different desired display and the user requested to relax so that 60% of the brainwave energy is below a frequency of 8 Hertz for a preselected time period. Again, the time to achieve this more relaxed criterion could be recorded. Feedback would be provided to the user when the desired state was reached and their ability to subsequently sustain that state can be measured by various statistical means. By repeating this procedure, the user can learn to make rapid and effective transitions between states of alertness in order to develop flexibility of attention. This training should help users achieve and sustain desired states of concentration and/or relaxation. By omitting the feedback from the procedure, the user's ability to flexibly switch his or her states of alertness or attention could be measured, for example, by deriving an average response time for several trials.

The foregoing detailed description is given primarily for clearness of understanding and no unnecessary limitations are to be understood therefrom for modifications will become obvious to those skilled in the art upon reading this disclosure and may be made without departing from the spirit of the invention or the scope of the appended claims.

What is claimed is:

1. A brainwave biofeedback apparatus to be worn by a user on the user's head, the apparatus comprising a scalp portion passing over a scalp of the user's head, said apparatus further comprising at least one scalp sensor unit, said at least one scalp sensor unit being detachably receivable by said scalp portion, said at least one scalp sensor unit having a scalp electrode cup and a compound sponge assembly, said scalp electrode cup including a scalp electrode having a scalp electrode lead extending therefrom, said compound sponge assembly including an absorbent sponge portion and a scalp contact and cleaning portion, said scalp contact and cleaning portion to engage said user's hair, said absorbent sponge portion being partway received by said scalp electrode cup, said scalp contact and cleaning portion being a layer external to said absorbent sponge portion and attached thereto.

2. The apparatus of claim 1, further comprising at least one earpiece, said at least one earpiece having an ear pad, said ear pad having a sensor receiving receptacle therein, said sensor receiving receptacle having an ear lobe sensor unit detachably received therein, said ear lobe sensor unit having a lobe electrode cup and a lobe sponge, said lobe electrode cup including a lobe electrode having a lobe electrode lead extending therefrom, said lobe sponge including an ear lobe engaging portion, said lobe sponge being partway received by said lobe electrode cup.

3. The apparatus of claim 2, where, when the user is wearing said apparatus, said ear lobe engaging portion of said lobe sponge and the user's respective ear lobe are in a flush relation.

4. The apparatus of claim 2, where said lobe sponge has a trapezoidal shaped cross-section, said ear lobe engaging portion including an upper portion to engage the user's ear lobe cartilage and a lower larger portion to engage the user's ear lobe fleshy portion.

5. The apparatus of claim 2, where said lobe electrode cup has a cup bottom, said cup bottom being in a first plane, said ear lobe engaging portion being in a second plane, said first and said second plane intersecting at a preselected angle.

6. The apparatus of claim 5, where said preselected angle is approximately fifteen degrees.

7. The apparatus of claim 1, where said scalp portion includes a headband, said headband having at least one extender connected thereto, said at least one extender detachably receiving said at least one scalp sensor unit.

8. The apparatus of claim 1, where said absorbent sponge portion comprises a dense sponge material.

9. The apparatus of claim 1 where said scalp contact and cleaning portion comprises a woven fiber material.

10. The apparatus of claim 2, further comprising an input/output interface unit, said lobe and said scalp electrode leads being received by said input/output interface unit.

11. The apparatus of claim 2, further comprising a signal processing unit, said signal processing unit receiving an electronic signal from each of said lobe and scalp electrode leads, said signal processing unit evaluating said electronic signals to determine a value representing an indication of alertness or relaxation.

12. The apparatus of claim 11, where said value is provided to a computer which processes said value and displays on a computer monitor an indication of alertness to the user.

13. The apparatus of claim 12, where said indication of alertness is a gauge which is more full with increased alertness.

14. The apparatus of claim 12, where said indication of alertness is a display which is more in focus with increased alertness.

15. The apparatus of claim 11, said at least one earpiece further comprising an earphone providing an audio signal to said user, where said value is provided to a computer which processes said value and alters said audio signal in response to said value to provide an indication of alertness to said user.

16. The apparatus of claim 15, where said indication of alertness is a volume change in said audio signal.

17. The apparatus of claim 16, where said indication of alertness is a clarity change in said audio signal.

18. The apparatus of claim 11, where said at least one scalp sensor unit comprises a first and a second scalp sensor unit, said scalp sensor units being detachably received by said scalp portion at preselected locations.

19. A brainwave biofeedback apparatus to be worn by a user on the user's head, the apparatus comprising a scalp portion passing over a scalp of the user's head, said apparatus further comprising at least one scalp sensor unit, said at least one scalp sensor unit being receivable by said scalp portion, said at least one scalp sensor unit having a scalp electrode cup and a compound sponge assembly, said scalp electrode cup including a scalp electrode having a scalp electrode lead extending therefrom, said compound sponge assembly including an absorbent sponge portion and a scalp contact and cleaning portion, said absorbent sponge portion being partway received by said scalp electrode cup, said scalp contact and cleaning portion being a layer external to said absorbent sponge portion and attached thereto.

20. The apparatus of claim 19, where said absorbent sponge portion comprises a dense sponge material and said scalp contact and cleaning portion comprises a woven fiber material.

* * * * *